United States Patent [19]

Sumita

[11] Patent Number: 5,082,803
[45] Date of Patent: Jan. 21, 1992

[54] PROCESS FOR PRODUCING BONE PROSTHESIS

[75] Inventor: Masaya Sumita, Tokyo, Japan

[73] Assignee: Asahi Kogaku Kogyo Kabushiki Kaisha, Tokyo, Japan

[21] Appl. No.: 586,101

[22] Filed: Sep. 21, 1990

[30] Foreign Application Priority Data

Sep. 21, 1989 [JP] Japan .................................. 1-245811

[51] Int. Cl.$^5$ ................................................ A61F 2/28
[52] U.S. Cl. .......................................... 501/1; 623/16
[58] Field of Search ............................... 501/1; 623/16

[56] References Cited

U.S. PATENT DOCUMENTS 4,080,213  3/1978  Mori et al. ...................... 106/38.5 R
4,938,938  7/1990  Ewers et al. ......................... 423/308

Primary Examiner—William R. Dixon, Jr.
Assistant Examiner—Chris Gallo
Attorney, Agent, or Firm—Sughrue, Mion, Zinn, Macpeak & Seas

[57] ABSTRACT

A process for producing a bone prosthesis is disclosed, which process comprises the steps of: (a) adding granular ceramics to pullulan; and (b) treating the granular ceramics and the pullulan with high-temperature and high-pressure steam.

6 Claims, No Drawings

PROCESS FOR PRODUCING BONE PROSTHESIS

FIELD OF THE INVENTION

The present invention relates to a process for producing a bone prosthesis and, more particularly to a process for producing a bone prosthesis having a block form.

BACKGROUND OF THE INVENTION

Application of calcium phosphate compounds, particularly hydroxyapatite as an artificial dental root, a bone prosthesis or a percutaneous device has been widely studied because of their excellent biocompatibility and capability of osteo-conductivity, and several kinds of these products have already been put into practical use. Bone prostheses include granules and pre-molded blocks. In particular, granular bone prostheses have been widely employed since they can be used to fill in a deficient part of any shape.

However, granular bone prostheses lack bonding properties among the granules thereof and are easily scattered and lost before they adhere to new bone. In order to overcome this disadvantage, a fibrin paste has been used to bond the granules to each other as described in JP-A-60-256460 and JP-A-60-256461 (the term "JP-A" as used herein means an "unexamined published Japanese patent application"). A fibrin paste, however, entertains a fear of infection with hepatitis virus, AIDS virus, etc. because it is prepared from human blood.

The present inventors have previously proposed a process for bonding granules containing α-tricalcium phosphate or tetracalcium phosphate as an essential component with an acid aqueous solution as disclosed in JP-A-2-1285 and EP-A-0324425. However, this technique is applicable only to those granules comprising α-tricalcium phosphate or tetracalcium phosphate.

The present inventors further proposed to use an aqueous solution of at least one of pullulan, glycol chitin, carboxymethyl chitin, and pectin, each of which does no harm to a living body, as a paste for bonding granules. This paste is suitable for in situ fixing of a granular bone prosthesis at the time of filling in a deficient part. However, such a paste is difficult to use to form pre-molded blocks from the granules because much time is required to evaporate the water content of the paste.

SUMMARY OF THE INVENTION

An object of the present invention is to provide a process for producing a bone prosthesis comprising bonding ceramic granules to each other, which process is easily carried out in a short time without involving removal of a water content.

Other objects and effects of the present invention will be apparent from the following description.

The present invention relates to a process for producing a bone prosthesis comprising the steps of (a) adding granular ceramics to pullulan; and (b) treating the granular ceramics and the pullulan with high-temperature and high-pressure steam.

DETAILED DESCRIPTION OF THE INVENTION

Unlike monosaccharides and oligosaccharides, polysaccharides generally have no melting point and undergo carbonization and pyrolysis on heating. Therefore, it is impossible to mix polysaccharides in a molten state with other substances in order to obtain a composite material as can be done with thermoplastic resins such as polyethylene.

In order to overcome this problem, the present inventor has conducted extensive researches in searching for a substance that can be liquified without being dissolved in a solvent, such as water, and can form a composite material with ceramic granules. As a result, the present inventor has found that pullulan which is only carbonized without melting on heating in the atmosphere can be liquefied under hightemperature and high-pressure steam and solidified at room temperature, and thus is capable of forming the desired composite material with ceramic granules. The present invention has been completed based on this finding.

Only pullulan that is liquefied in high-temperature and high-pressure steam, but other polysaccharides (e.g., carboxymethyl chitin, glycol chitin, and pectin) are not liquefied. The reason why only pullulan is liquified in high-temperature and high-pressure steam has not yet been clarified. In the present invention, however, since pullulan becomes liquid without using any solvent, such a change of condition is expressed by the terminology "liquefaction". The use of this terminology is not intended to limit the present invention in any way.

The molecular weight, the form and the like properties of pullulan used in the present invention are not particularly limited. It is preferred to use pullulan purified by removing cell bodies, salts, proteins and other impurities. The form of pullulan may be powder, a sheet, a block and the like. Commercially available pullulan, which is purified pullulan in the form of powder, a sheet or the like, may be used in the present invention.

In the present invention, granular ceramics can be used as a bone prosthesis material. Examples of the ceramics include calcium phosphate ceramics, alumina ceramics, and zirconia ceramics. Specific examples of the granular ceramics are described, e.g., in U.S. Pat. No. 4,693,986, 4,097,935 and 4,629,464. Preferred examples of the ceramics include calcium phosphate ceramics, such as ceramics comprising at least one of hydroxyapatite, fluorapatite, α-tricalcium phosphate, β-tricalcium phosphate, and tetracalcium phosphate.

The diameter of the granular ceramics is preferably from 1 μm to 6 mm. In the case where a relatively large bone prosthesis for orthopedic use, etc. is prepared, the diameter of the granular ceramics is preferably from 600 μm to 6 mm. In the case where a relatively small bone prosthesis for periodontic use, etc. is prepared, the diameter of the granular ceramics is preferably from 1 to 300 μm.

Granules of ceramics can be prepared, for example, by conventional manners as described in U.S. Pat. Nos. 4,693,986, 4,097,935 and 4,629,464, such as a spray drying process, a granulation process by high-speed stirring, a process of grinding a ceramic block, a process of grinding a compressed powder, and a process of grinding a cake prepared using a wet process. If desired, the thus prepared granules may be calcined, or a calcined material may be granulated.

The granules may be either dense or porous, and porous granules are preferred in view of the biocompatibility.

The amount of pullulan to be used varies depending on the kind of the ceramics and can be appropriately determined by one skilled in the art. In general, the weight ratio of calcium phosphate or alumina ceramic granules to pullulan preferably ranges from 0.1 to 10 by weight. The weight ratio of zirconia ceramic granules to pullulan preferably ranges from 0.18 to 17.7 by weight.

The method for addition of granular ceramics to pullulan is not particularly limited. For example, the granular ceramics is added and mixed with powdered pullulan, or the granular ceramics is simply added to powdered, sheetshaped or block-shaped pullulan without mixing. It is preferred that the granular ceramics and powdered pullulan is mixed to form a mixture. The mixing can be carried out, e.g., by simply stirring the ingredients in a vessel with a stick. Although the granular ceramics and pullulan is simply added to pullulan without mixing, a bone prosthesis is finally obtained as a composite material in which the granular ceramics and pullulan are in the mixed state by the subsequent treatment with high-temperature and high-pressure steam. Pullulan may previously treated with high-temperature and high-pressure steam before the addition of the granular ceramics, and the granular ceramics may be added to liquified pullulan at an elevated temperature or to solidified pullulan at room temperature.

The granular ceramics and pullulan, which may be mixed or not mixed, subjected to treatment with hightemperature and high-pressure steam. The high-temperature and high-pressure steam atmosphere can be established most conveniently by utilizing an autoclave such as those for medical use. Most of the autoclaves for medical use are set at from 115° C. in temperature and 0.7 kg/cm$^2$ in pressure to 132° C. in temperature and 2 kg/cm$^2$ in pressure, and any temperature and pressure conditions inside this range can preferably be employed. Although the temperature and pressure are set at the predetermined condition, pullulan is liquified to some extent during the course of the temperature increment from the atmospheric condition to the predetermined condition. The treatment is carried out for a time sufficient for pullulan to be liquefied and to wet the surrounding granules.

After the high-temperature and high-pressure treatment, the mixture is cooled to about room temperature to obtain a bone prosthesis comprising the ceramic granules bonded by solidified pullulan.

The bone prosthesis can be shaped by that the granular ceramics and pullulan are treated with high-temperature and high-pressure steam in a container having a desired shape. The resulting bone prosthesis may further be shaped by cutting with a knife, a diamond bar, etc.

In preparing the bone prosthesis according to the present invention, previously sterilized raw materials may be used, or a finished bone filler may be sterilized. Methods of sterilization are not particularly limited. However, the process of the present invention itself produces a sterilized product and a separate sterilization step may be omitted.

The present invention is now illustrated in greater detail with reference to Examples, but it should be understood that the present invention is not deemed to be limited thereto.

EXAMPLE 1

Five grams of a commercially available hydroxyapatite granules ("Apaceram G-S" produced by Asahi Kogaku Kogyo K.K. diameter: 300 to 600 μm) and 5 g of powdered pullulan ("PI-20" produced by Hayashibara K.K., molecular weight: 200,000) were mixed with a PTFE stick in a polypropylene container (inner diameter: 35 mm, depth: 15 mm), and the mixture in the container was treated in an autoclave for medical use ("Sterimight 18A" produced by Hirayama Seisakusho K.K.) set at 132° C. and 2 kg/cm$^2$ for 1 minute. After cooling, the mixture was taken out to obtain a composite bone prosthesis in which pullulan and the granules were integrally solidified.

EXAMPLE 2

The same procedures as in Example 1 were repeated except that the commercially available hydroxyapatite granules was replaced with granular hydroxyapatite (average diameter: about 20 μm, specific surface area: about 55 cm$^2$/g) which was prepared by spray drying a hydroxyapatite slurry synthesized by using a calcium hydroxide slurry and a phosphoric acid aqueous solution according to a conventional wet process. The product obtained was a solidified composite bone prosthesis similar to that produced in Example 1.

EXAMPLE 3

Two grams of pullulan ("PI-20") was placed in a polyethylene container (inner diameter: 40 mm, depth: 7 mm) and treated in an autoclave used in Example 1 under the same conditions as in Example 1 except that the treatment time was changed to 10 minutes. The pullulan was once liquified and then solidified at room temperature. Two grams of hydroxyapatite granules ("Apaceram G-M", diameter: 600 to 1,000 μm) were added to the solidified pullulan such that the granules were placed on the solidified pullulan, and then treated in an autoclave used in Example 1 under the same conditions as in Example 1 except that the treatment time was changed to 10 minutes. As a result, a composite bone prosthesis (diameter: 40 mm, thickness: 2 mm) in which pullulan and granules were integrally solidified was obtained.

COMPARATIVE EXAMPLE 1

The same procedure as in Example 1 was repeated except that an electric furnace set at 132° C. in place of the autoclave for medical use was used. As a result, pullulan was not liquefied, and a composite bone prosthesis was not obtained.

COMPARATIVE EXAMPLE 2

The same procedure as in Example 1 was repeated except that an electric furnace set at 240° C. was used in place of the autoclave for medical use, and an alumina crucible was used in place of the polypropylene container. As a result, the pullulan underwent color change but was not liquefied, and a composite bone prosthesis was not obtained.

According to the present invention, ceramic granules can be bonded and fixed together very easily in a short time without requiring removal of the water content by using a material causing no harm to a living body. Since the process according to the present invention uses high-temperature and high-pressure steam, the process achieves sterilization simultaneously with bonding.

While the invention has been described in detail and with reference to specific embodiments thereof, it will be apparent to one skilled in the art that various changes and modifications can be made therein without departing from the spirit and scope thereof.

What is claimed is:

1. A process for producing a bone prosthesis comprising the steps of: (a) adding granular ceramics to pullulan; and (b) treating said granular ceramics and said pullulan with high-temperature and high-pressure steam.

2. A process as claimed in claim 1, said process comprising the steps of: (a) mixing granular ceramics with powdered pullulan to form a mixture; and (b) treating said mixture with high-temperature and high-pressure steam.

3. A process as claimed in claim 1, wherein said ceramics is a calcium phosphate ceramics.

4. A process as claimed in claim 1, wherein said ceramics is ceramics comprising at least one of hydroxyapatite, fluorapatite, $\alpha$-tricalcium phosphate, $\beta$-tricalcium phosphate, and tetracalcium phosphate.

5. A process as claimed in claim 1, wherein a mixing ratio of said granular ceramics to said pullulan is from 0.1 to 10 by weight.

6. A process as claimed in claim 1, wherein said step of treating said mixture with high-temperature and highpressure steam is carried out by using an autoclave.

* * * * *